(12) United States Patent
Kaneko et al.

(10) Patent No.: US 12,721,966 B2
(45) Date of Patent: Sep. 1, 2026

(54) MEDICAL SHAFT, MEDICAL DEVICE, AND METHOD FOR MANUFACTURING MEDICAL SHAFT

(71) Applicant: KANEKA CORPORATION, Osaka (JP)

(72) Inventors: Takuya Kaneko, Okaya (JP); Yuki Mukai, Okaya (JP)

(73) Assignee: KANEKA CORPORATION, Osaka (JP)

( * ) Notice: Subject to any disclaimer, the term of this patent is extended or adjusted under 35 U.S.C. 154(b) by 973 days.

(21) Appl. No.: 17/801,562

(22) PCT Filed: Jan. 22, 2021

(86) PCT No.: PCT/JP2021/002263
§ 371 (c)(1),
(2) Date: Aug. 23, 2022

(87) PCT Pub. No.: WO2021/171849
PCT Pub. Date: Sep. 2, 2021

(65) Prior Publication Data

US 2023/0079356 A1 Mar. 16, 2023

(30) Foreign Application Priority Data

Feb. 26, 2020 (JP) ................................ 2020-030645

(51) Int. Cl.
*A61M 25/00* (2006.01)
*A61L 29/02* (2006.01)
(Continued)

(52) U.S. Cl.
CPC ......... *A61M 25/0026* (2013.01); *A61L 29/02* (2013.01); *A61L 29/041* (2013.01); *A61M 25/0009* (2013.01); *C08L 23/06* (2013.01)

(58) Field of Classification Search
CPC ...................... A61M 25/0026; A61M 25/0009
See application file for complete search history.

(56) References Cited

U.S. PATENT DOCUMENTS 8,900,263 B2 * 12/2014 Fortson ............. A61B 17/3415 606/108
2002/0007145 A1 * 1/2002 Stivland ............. A61M 25/104 604/103
(Continued)

FOREIGN PATENT DOCUMENTS

EP 0595308 A2 * 5/1994 ........ A61M 25/1036
EP 1679094 B1 * 4/2008 ............ B29D 23/00
(Continued)

OTHER PUBLICATIONS

Machine translation JP2013132432A (Year: 2013).*
(Continued)

*Primary Examiner* — Abbas Rashid
*Assistant Examiner* — Wayne K. Swier
(74) *Attorney, Agent, or Firm* — Birch, Stewart, Kolasch & Birch, LLP

(57) ABSTRACT

A medical shaft includes a shaft including at least one lumen extending in a longitudinal direction; a core member disposed in the lumen, the core member extending along the longitudinal direction; and a tubular member disposed on an outer side of the core member in a same lumen as a lumen in which the core member is disposed, the tubular member having a length, in the longitudinal direction, which is less than a length of the core member, wherein in the lumen, an area of a cross-section of the lumen on a plane perpendicular to the longitudinal direction in a portion in which the tubular member is disposed is greater than an area of a cross section
(Continued)

of the lumen on a plane perpendicular to the longitudinal direction in a portion in which the tubular member is not disposed.

9 Claims, 4 Drawing Sheets

(51) Int. Cl.
*A61L 29/04* (2006.01)
*C08L 23/06* (2006.01)

(56) References Cited

U.S. PATENT DOCUMENTS

2006/0036233 A1* 2/2006 Boutillette ........ A61M 25/0169 604/528
2008/0287786 A1 11/2008 Lentz
2010/0217372 A1 8/2010 Lentz
2011/0172520 A1 7/2011 Lentz
2013/0046199 A1* 2/2013 Dubois ............ A61B 17/32002 600/566

FOREIGN PATENT DOCUMENTS

EP 3329958 A1 * 6/2018 ........ A61M 25/0045
JP 2010-527258 A 8/2010
JP 2013132432 A * 7/2013 ............... A23B 7/10
JP 2013-233202 A 11/2013
JP 2014-36732 A 2/2014
WO WO-8500008 A1 * 1/1985 ............. A61B 17/11
WO WO-9516477 A1 * 6/1995 .......... A61M 25/001

OTHER PUBLICATIONS

Machine translation JP2013233202A (Year: 2013).*
Machine translation JP2014036732A (Year: 2014).*
International Search Report, issued in PCT/JP2021/002263, mailed Mar. 23, 2021.

* cited by examiner

[Fig.1]
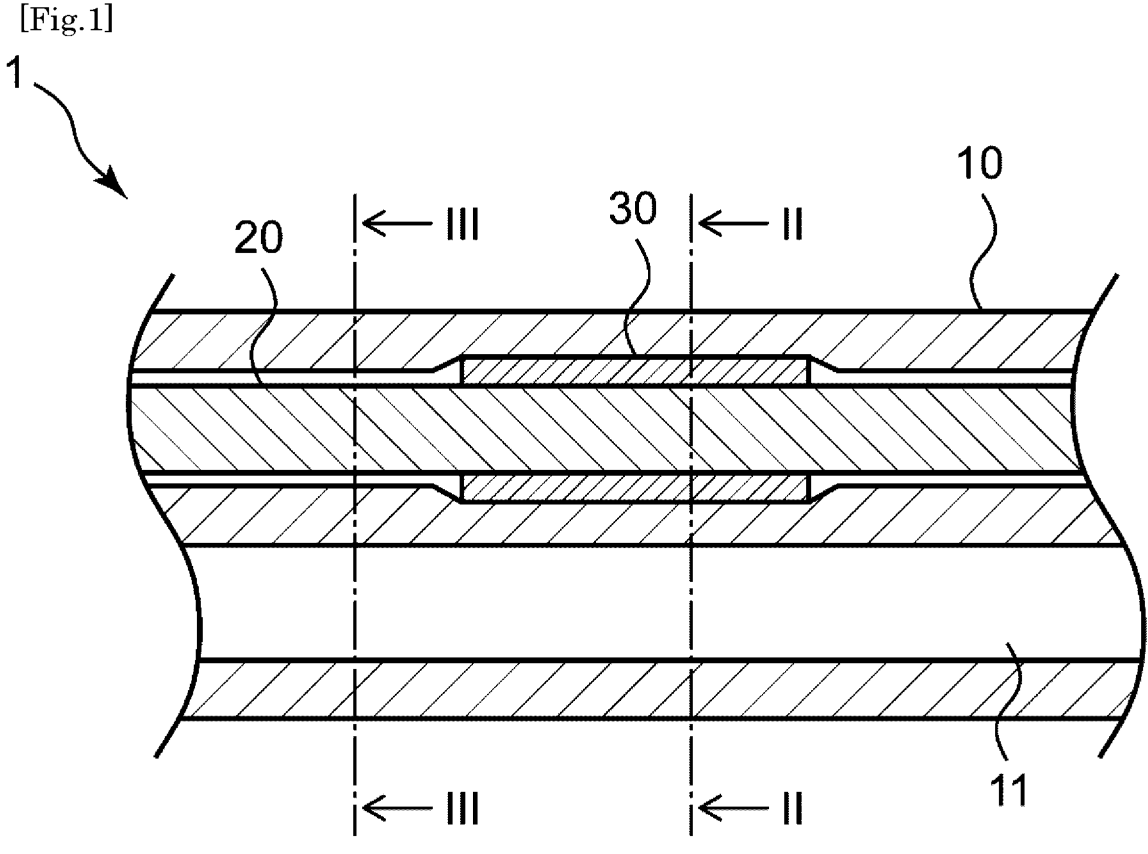
[Fig.2]
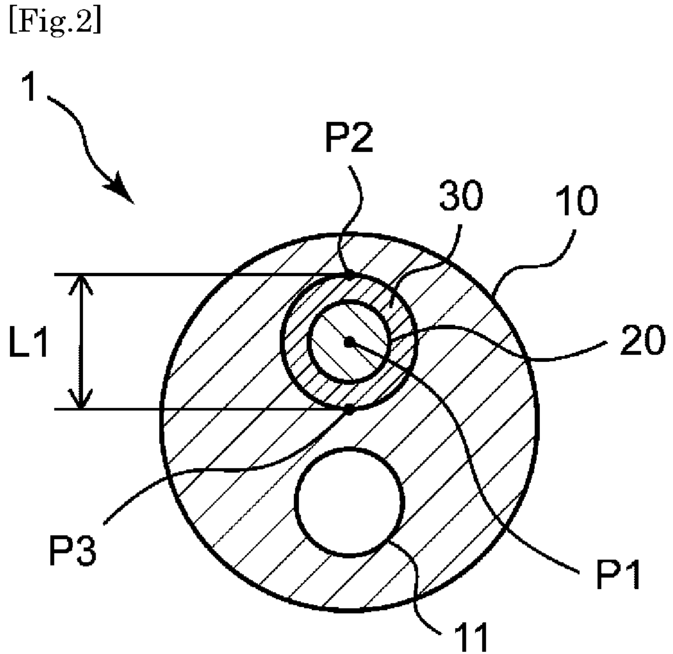

[Fig.3]
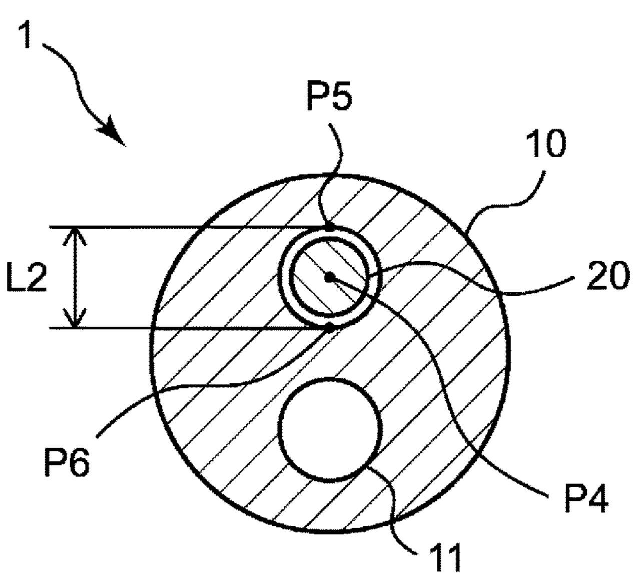
[Fig.4]
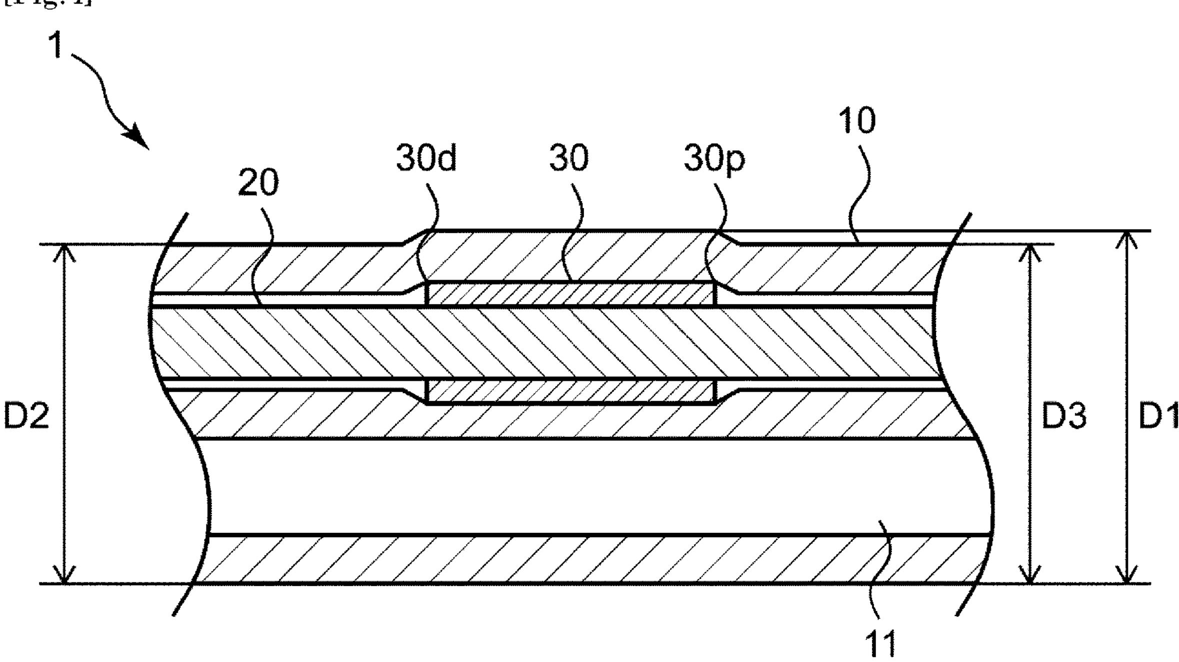

[Fig.5]
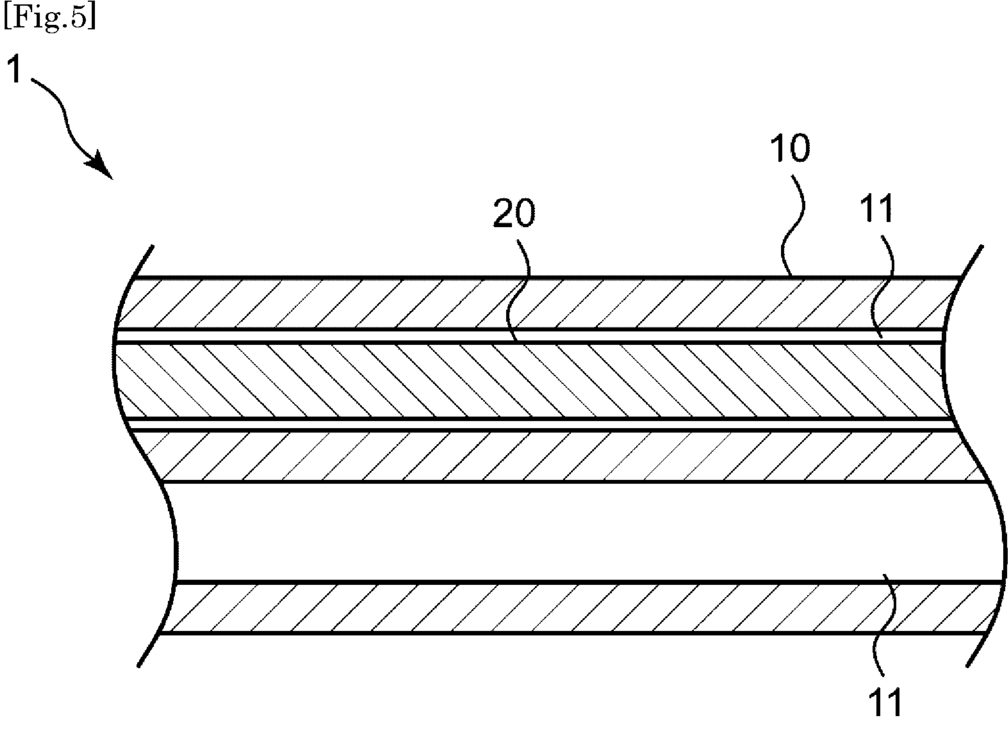
[Fig.6]
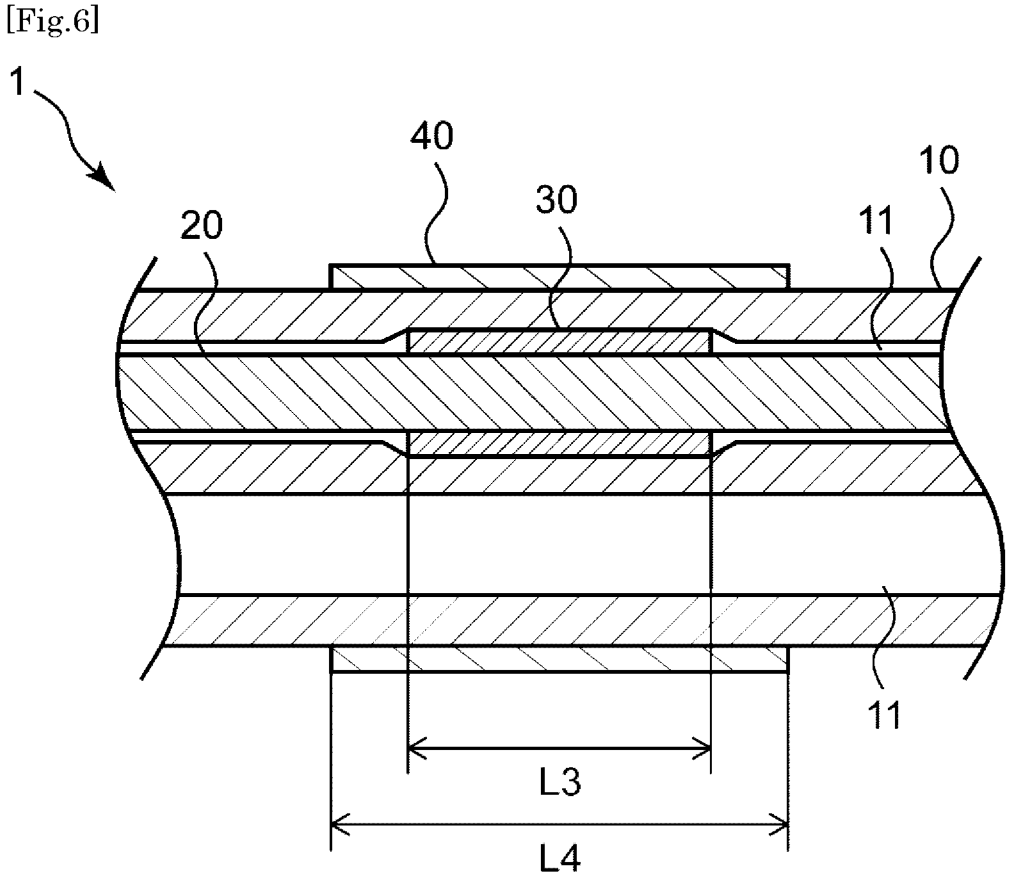

[Fig.7]
1
10
50
11
11
[Fig.8]
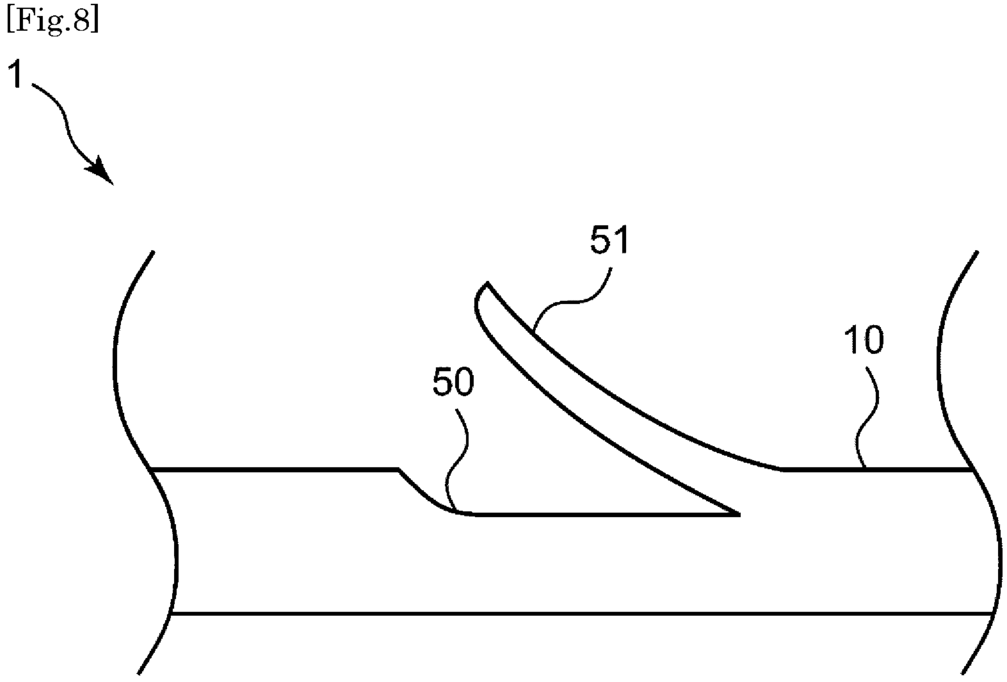

MEDICAL SHAFT, MEDICAL DEVICE, AND METHOD FOR MANUFACTURING MEDICAL SHAFT

TECHNICAL FIELD

The present invention relates to a medical shaft having a core member disposed in a lumen, a medical device including the medical shaft, and a method for manufacturing the medical shaft.

BACKGROUND ART

A catheter has a shaft to be inserted in a lumen such as a blood vessel and a gastrointestinal tract in a body. The catheter to be inserted in a narrow lumen in the body preferably has a small outer diameter. The catheter is preferably flexible for inserting the catheter deeply into the complex lumen. Meanwhile, when the catheter is inserted in the lumen, the catheter is operated so as to be pushed or rotated from a hand side of the catheter outside the body. Therefore, the catheter is required to have a certain hardness in order to transmit a force generated by the operation to the leading end of the catheter. In some catheters, core members are disposed in lumens in order to impart stiffness to the shafts.

By operating the catheter, the shaft of the catheter is subjected to a tensile force or a compressive force in the shaft longitudinal direction. When the catheter is conveyed to a desired place, the shaft is also subjected to a force in a rotating direction (torsion) for controlling the orientation of the catheter and a direction in which the leading end is directed. Therefore, the shaft and each member such as a core member need to be firmly fixed to each other.

For example, Patent Literature 1 discloses a catheter that includes a distal shaft on the distal side, a proximal shaft on the proximal side, a core wire that is disposed in a shaft lumen and that has a base end side portion fixed to an inner circumferential surface of the proximal shaft and has a leading end side portion tapered toward the leading end, and a resisting member which is fixed in a leading-end-side shaft member so as to be in contact with the core wire and in which a sliding resistance with respect to the core wire is higher than that of the distal shaft and higher than that of an inner shaft. In the catheter, the resisting member is formed in a cylindrical shape and fixed to the outer side of the inner shaft, to form a narrow portion in the lumen, and the leading end side portion of the core wire is inserted through the narrow portion, and the catheter has an engagement-stop portion having a diameter greater than a diameter of a gap of the narrow portion, in a portion closer to the base end side than the narrow portion is. Patent Literature 2 discloses a tubular medical shaft to be used in a state where a linear core wire is fixed to the medical shaft, the medical shaft including a leading end portion in which a helical slit is formed from the leading end edge toward the base end side, a notch formed at a part of the leading end edge including no slit so as to occupy a portion that is not greater than 50% of the entire circumference of the medical shaft, and a fixing region used for fixing the core wire to an inner wall opposing the notch.

CITATION LIST

Patent Literature

PATENT LITERATURE 1: Japanese Unexamined Laid-open Patent Application Publication No. 2014-036732

PATENT LITERATURE 2: Japanese Unexamined Laid-open Patent Application Publication No. 2013-233202

SUMMARY OF INVENTION

Technical Problem

In a conventional catheter and a conventional method for manufacturing a catheter, an adhesive is not easily filled between the shaft and an outer circumference of the core member when the core member or the like is fixed to the shaft, and sufficient joining of the shaft and the entire outer circumference of the core member to each other is difficult, and sufficient enhancement of a strength of joining the core member and the shaft to each other is difficult. Therefore, as disclosed in Patent Literatures 1 and 2, a catheter in which a shaft and a core member are engaged with and joined to each other, and a catheter in which a state in which the shaft and the core member are joined to each other can be checked, have been structured. However, for the catheters as disclosed in Patent Literatures 1 and 2, the number of process steps of joining the core member and the shaft to each other is increased, and, furthermore, a lot of restrictions are placed on the size of each member such as an inner diameter and an outer diameter of another member for joining, an outer diameter of the core member, and an inner diameter of the lumen of the shaft, and it is difficult to conform the sizes to, for example, usage of the catheter.

The present invention has been made in view of the aforementioned circumstances, and an object of the present invention is to provide a medical shaft in which strength of joining a core member and a shaft to each other is high, a medical device that includes the medical shaft, and a method for manufacturing the medical shaft in which the core member and the shaft are easily joined firmly to each other.

Solution to Problem

A medical shaft, which solves the above problem, comprises: a shaft including at least one lumen extending in a longitudinal direction; a core member disposed in the lumen, the core member extending along the longitudinal direction; and a tubular member disposed on an outer side of the core member in a same lumen as a lumen in which the core member is disposed, the tubular member having a length, in the longitudinal direction, which is less than a length of the core member, wherein in the lumen, an area of a cross-section of the lumen on a plane perpendicular to the longitudinal direction in a portion in which the tubular member is disposed is greater than an area of a cross section of the lumen on a plane perpendicular to the longitudinal direction in a portion in which the tubular member is not disposed.

In the medical shaft of the present invention, it is preferable that a material of the core member is a metal, and a material of the tubular member is a resin composition containing polyethylene as a main component.

In the medical shaft of the present invention, it is preferable that an outer diameter of the shaft in the portion in which the tubular member is disposed is greater than an outer diameter of the shaft in a portion closer to a distal side than a distal end of the tubular member is, and is greater than an outer diameter of the shaft in a portion closer to a proximal side than a proximal end of the tubular member is.

In the medical shaft of the present invention, it is preferable that an outer diameter of the shaft in the portion in which the tubular member is disposed is less than an outer diameter of the shaft in a portion closer to a distal side than a distal end of the tubular member is, and is less than an outer diameter of the shaft in a portion closer to a proximal side than a proximal end of the tubular member is.

In the medical shaft of the present invention, it is preferable that in the lumen, a length of a major axis of a cross-section of the tubular member on a plane perpendicular to the longitudinal direction in the portion in which the tubular member is disposed is greater than a length of a major axis of a cross-section of the lumen on a plane perpendicular to the longitudinal direction in the portion in which the tubular member is not disposed.

In the medical shaft of the present invention, it is preferable that a plurality of the tubular members are disposed at different positions in the lumen.

In the medical shaft of the present invention, it is preferable that the length of the tubular member in the longitudinal direction is not greater than 1/10 of the length of the core member.

In a medical device of the present invention, it is preferable that comprising the medical shaft.

A method for manufacturing a medical shaft, which solves the above problem, comprises: a shaft including at least one lumen extending in a longitudinal direction; a core member disposed in the lumen, the core member extending along the longitudinal direction; and a tubular member disposed between the shaft and the core member in a same lumen as a lumen in which the core member is disposed, the tubular member having a length, in the longitudinal direction, which is less than a length of the core member, the method comprising: disposing, in the lumen of the shaft, the core member on which the tubular member is not disposed; disposing the core member inside the tubular member; and heating the tubular member.

In the method for manufacturing a medical shaft of the present invention, it is preferable that an outer diameter of the tubular member is greater than an inner diameter of the lumen before the disposing of the core member in the lumen of the shaft.

In the method for manufacturing a medical shaft of the present invention, it is preferable that further comprising disposing an outer tubular member outward of the shaft in a portion in which the tubular member is disposed after the disposing of the core member inside the tubular member and the disposing of the core member having the tubular member disposed thereon in the lumen of the shaft.

In the method for manufacturing a medical shaft of the present invention, it is preferable that the heating of the tubular member includes heating the shaft in the portion in which the tubular member is disposed.

In the method for manufacturing a medical shaft of the present invention, it is preferable that further comprising heating the shaft at a temperature of not lower than 50° C. for two hours or longer after the heating of the tubular member.

In the method for manufacturing a medical shaft of the present invention, it is preferable that further comprising forming an opening through which the lumen and a portion outside the shaft are connected.

In the method for manufacturing a medical shaft of the present invention, it is preferable that an outer surface of the shaft is cut to form a flap in which one of end portions is a free end and another of the end portions is integrated with the shaft, in the forming of the opening.

In the method for manufacturing a medical shaft of the present invention, it is preferable that further comprising disposing the core member in the lumen of the shaft before the disposing of the core member inside the tubular member, wherein the forming of the opening is performed after the disposing of the core member in the lumen of the shaft, and the outer surface of the shaft is cut in the forming of the opening in a state where the core member is disposed in the lumen.

Advantageous Effects of Invention

In the medical shaft of the present invention, since the area of the cross-section of the lumen on the plane perpendicular to the longitudinal direction in the portion in which the tubular member is disposed is greater than the area of the cross-section of the lumen on the plane perpendicular to the longitudinal direction in the portion in which the tubular member is not disposed, the outer surface of the tubular member is pressed against the wall surface of the lumen of the shaft in the portion in which the tubular member is disposed. Therefore, the tubular member easily comes into close contact with the wall surface of the lumen of the shaft, and the core member and the shaft can be firmly joined to each other through the tubular member. The method for manufacturing the medical shaft according to the present invention includes: disposing the core member inside the tubular member; disposing the core member in the lumen of the shaft; and heating the tubular member. Therefore, the core member and the shaft can be easily joined firmly to each other through the tubular member.

BRIEF DESCRIPTION OF DRAWINGS

FIG. 1 shows a cross-sectional view, along a longitudinal direction, of a medical shaft according to one embodiment of the present invention.

FIG. 2 shows a cross-sectional view of the medical shaft shown in FIG. 1 as taken along II-II.

FIG. 3 shows a cross-sectional view of the medical shaft shown in FIG. 1 as taken along III-III.

FIG. 4 shows a cross-sectional view, along a longitudinal direction, of a medical shaft according to another embodiment of the present invention.

FIG. 5 shows a cross-sectional view, along the longitudinal direction, of the medical shaft in a state where a core member is disposed in a lumen of the shaft, in a method for manufacturing the medical shaft according to one embodiment of the present invention.

FIG. 6 shows a cross-sectional view, along the longitudinal direction, of the medical shaft in a state where an outer tubular member is disposed outward of the shaft in a portion in which a tubular member is disposed, in the method for manufacturing the medical shaft according to one embodiment of the present invention.

FIG. 7 shows a cross-sectional view, along the longitudinal direction, of the medical shaft in a state of having an opening through which the lumen and a portion outside the shaft are connected, in the method for manufacturing the medical shaft according to one embodiment of the present invention.

FIG. 8 shows a view, along the longitudinal direction, of the medical shaft in a state where the shaft has a flap formed therein, in the method for manufacturing the medical shaft according to one embodiment of the present invention.

DESCRIPTION OF EMBODIMENTS

Hereinafter, the present invention is specifically described below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

FIG. 1 is a cross-sectional view, along a longitudinal direction, of a medical shaft 1 according to one embodiment of the present invention. FIG. 2 is a cross-sectional view of the medical shaft 1 shown in FIG. 1 as taken along II-II. FIG. 3 is a cross-sectional view of the medical shaft 1 shown in FIG. 1 as taken along III-III.

As shown in FIG. 1 to FIG. 3, the medical shaft 1 of the present invention includes a shaft 10 having at least one lumen 11 extending in the longitudinal direction, a core member 20 disposed in the lumen 11 so as to extend along the longitudinal direction, and a tubular member 30 disposed on the outer side of the core member 20.

In the present invention, the proximal side refers to a user's hand side with respect to the direction in which the shaft 10 extends, and the distal side refers to the side opposite to the proximal side, that is, a to-be-treated subject side. The direction in which the shaft 10 extends is referred to as a longitudinal direction. In other words, the longitudinal direction is a distal-proximal direction of the shaft 10. Radial direction refers to a direction of a radius of a circumcircle of a cross-sectional shape in the longitudinal direction of the shaft 10, radially inward refers to a direction toward the axial center of the circumcircle of the cross-sectional shape of the shaft 10, and radially outward refers to a direction toward the side opposite to the inward direction side.

The shaft 10 has at least one lumen 11 extending in the longitudinal direction. Although the number of the lumens 11 in the shaft 10 may be one, the number thereof is preferably plural. In a case where the shaft 10 includes a plurality of the lumens 11, for example, the lumen 11 used as a path through which a guide wire is inserted, the lumen 11 into which a contrast agent or drug is injected, and the lumen 11 serving as a flow path of fluid used for expanding a balloon in a case where the balloon is connected to the shaft 10, can be separately disposed in addition to the lumen 11 in which the core member 20 is disposed. Therefore, the medical shaft 1 can be functionally structured. The medical shaft 1 can be used for various medical devices. Examples of the medical device include a catheter, devices for endoscopes, high-frequency devices, and ultrasonic devices.

Examples of a material of the shaft 10 include polyamide-based resins, polyester-based resins such as polyethylene terephthalate, polyurethane-based resins, polyolefin-based resins such as polyethylene, polypropylene, and vinyl chloride, fluorine-based resins such as polytetrafluoroethylene, silicone-based resins, and natural rubber. One of them may be used alone or two or more of them may be used in combination. Among them, the material of the shaft 10 is preferably at least one of polyamide-based resin, polyolefin-based resin, and fluorine-based resin. In a case where the material of the shaft 10 is at least one of polyamide-based resin, polyolefin-based resin, and fluorine-based resin, slidability of the surface of the shaft 10 can be enhanced, and insertability with respect to a blood vessel can be enhanced.

The cross-sectional shape of the shaft 10 in the longitudinal direction may be a round shape, an ellipsoidal shape, a polygonal shape, or a combination thereof. The cross-sectional shape of the lumen 11 in the longitudinal direction may also be a round shape, an ellipsoidal shape, a polygonal shape, or a combination thereof.

As shown in FIG. 1, the core member 20 is disposed in the lumen 11, and extends along the longitudinal direction of the shaft 10. Since the shaft 10 has the core member 20, stiffness of the shaft 10 can be enhanced in a portion in which the core member 20 is disposed.

A material of the core member 20 is, for example, a metal such as stainless steel and Ni—Ti alloy, and synthetic resin the examples of which include polyolefin-based resins such as polyethylene and polypropylene, polyamide-based resins such as nylon, polyester-based resins such as PET, aromatic polyether ketone-based resins such as PEEK, polyether-polyamide-based resins, polyurethane-based resins, polyimide-based resins, and fluorine-based resins such as PTFE, PFA, and ETFE.

The material of the core member 20 preferably has stiffness higher than the material of the shaft 10. In a case where the stiffness of the material of the core member 20 is higher than the stiffness of the material of the shaft 10, the stiffness of the shaft 10 is likely to be enhanced when the core member 20 is disposed in the lumen 11 of the shaft 10.

Although the core member 20 may have a tubular shape having an inner cavity extending in the longitudinal direction, the core member 20 is preferably a solid object having no inner cavity. In a case where the core member 20 is solid, the stiffness of the core member 20 can be enhanced without increasing the outer diameter of the core member 20. Therefore, in a case where the core member 20 is disposed in the lumen 11, the stiffness of the shaft 10 can be sufficiently enhanced.

The core member 20 may be formed of a single wire or a twisted wire obtained by twisting single wires. Among them, the core member 20 is preferably formed of a single wire. In a case where the core member 20 is formed of a single wire, slidability of the outer surface of the core member 20 is enhanced, and the core member 20 is easily disposed in the lumen 11.

The cross-sectional shape of the core member 20 in the longitudinal direction may be a round shape, an ellipsoidal shape, a polygonal shape, or a combination thereof. Among them, the cross-sectional shape of the core member 20 in the longitudinal direction is preferably a round shape or an ellipsoidal shape. In a case where the cross-sectional shape of the core member 20 is a round shape or an ellipsoidal shape, the circumferential wall of the lumen 11 can be inhibited from being damaged by the core member 20 when the core member 20 is disposed in the lumen 11, and, furthermore, the inner surface of the tubular member 30 can be inhibited from being damaged by the core member 20 when the tubular member 30 is disposed on the outer side of the core member 20.

As shown in FIG. 1, the tubular member 30 is disposed in the same lumen 11 as the lumen 11 in which the core member 20 is disposed, and is disposed on the outer side of the core member 20. Since the tubular member 30 is disposed on the outer side of the core member 20, the tubular member 30 comes into contact with the outer surface of the core member 20 and the circumferential wall of the lumen 11, and the core member 20 and the lumen 11 can be fixed through the tubular member 30. The tubular member 30 is disposed between the shaft 10 and the core member 20, and a length of the tubular member 30 in the longitudinal direction is less than the length of the core member 20.

A material of the tubular member 30 is, for example, synthetic resin the examples of which include polyethylene such as high-density polyethylene, low-density polyethylene, and linear low-density polyethylene, and polyolefin-based resins such as polypropylene.

The cross-sectional shape of the tubular member 30 in the longitudinal direction may be a C-shape or a rolled shape. The C-shaped cross-sectional shape represents a state where the tubular member 30 has a slit extending in the longitudinal direction of the shaft 10 and the cross-sectional shape is not closed. The rolled cross-sectional shape represents a state where the tubular member 30 is sheet-shaped, and end portions of the sheet extending in the longitudinal direction of the shaft 10 are in contact with each other to wrap the core member 20. The cross-sectional shape of the outer shape of the tubular member 30 in the longitudinal direction may also be a round shape, an ellipsoidal shape, a polygonal shape, or a combination thereof.

A length of the tubular member 30 in the longitudinal direction is less than a length of the core member 20. Since the length of the tubular member 30 is less than the length of the core member 20, the shaft 10 and the core member 20 can be efficiently fixed by using the tubular member 30.

In the lumen 11, an area of the cross-section of the lumen 11 on the plane perpendicular to the longitudinal direction in a portion in which the tubular member 30 is disposed as shown in FIG. 2, is greater than an area of the cross-section of the lumen 11 on the plane perpendicular to the longitudinal direction in a portion in which the tubular member 30 is not disposed as shown in FIG. 3. The area of the cross-section of the lumen 11 refers to an area of a region surrounded by the circumferential wall of the lumen 11 on the cross-section perpendicular to the longitudinal direction. In a case where the area of the cross-section of the lumen 11 on the plane perpendicular to the longitudinal direction in the portion in which the tubular member 30 is disposed is greater than the area of the cross-section of the lumen 11 on the plane perpendicular to the longitudinal direction in the portion in which the tubular member 30 is not disposed, the outer surface of the tubular member 30 is pressed against the circumferential wall of the lumen 11 such that the lumen 11 is press-widened by the tubular member 30 disposed on the outer side of the core member 20. Therefore, the tubular member 30 comes into close contact with the lumen 11 of the shaft 10, and the tubular member 30 can be firmly joined to the shaft 10. That is, the core member 20 and the shaft 10 can be firmly joined to each other through the tubular member 30.

The area of the cross-section of the lumen 11 on the plane perpendicular to the longitudinal direction in the portion in which the tubular member 30 is disposed is made greater than the area of the cross-section of the lumen 11 on the plane perpendicular to the longitudinal direction in the portion in which the tubular member 30 is not disposed when, for example, the outer diameter of the tubular member 30 is set so as to be greater than the diameter of the lumen 11 as shown in FIG. 1 and FIG. 2. In a case where the outer diameter of the tubular member 30 is made greater than the diameter of the lumen 11, the outer surface of the tubular member 30 is pressed against the circumferential wall of the lumen 11 when the tubular member 30 is disposed in the lumen 11, and the area of the cross-section of the lumen 11 on the plane perpendicular to the longitudinal direction in the portion in which the tubular member 30 is disposed can be made greater than the area of the cross-section of the lumen 11 in the portion in which the tubular member 30 is not disposed.

The shape of a lumen (hereinafter, may also be referred to as "empty lumen") other than the lumen 11 in which the core member 20 is disposed as shown in FIG. 1 is preferably formed such that the lumen 11 has a constant cross-section regardless of a portion corresponding to the portion in which the tubular member 30 is disposed on the core member 20 in the lumen 11 in which the core member 20 is disposed, and a portion corresponding to the portion in which the tubular member 30 is not disposed in the lumen 11 in which the core member 20 is disposed. A protective core member for protecting the empty lumen may be disposed in the empty lumen in the manufacturing process in order to obtain a constant cross-sectional shape. In a case where the protective core member is disposed in the empty lumen, a length of the major axis of the cross-sectional shape of the empty lumen can be assured. Furthermore, in a step of heating the shaft 10 in order to join the core member 20 and the shaft 10 to each other, escape of stress in the case of the shaft 10 being melted or softened is prevented and the tubular member 30 comes into closer contact with the core member 20 to further enhance joining strength.

As shown in FIG. 1, the maximum outer diameter of the core member 20 is preferably less than the minimum inner diameter of the lumen 11 in which the core member 20 is disposed. In a case where the maximum outer diameter of the core member 20 is less than the minimum inner diameter of the lumen 11, the core member 20 can be more easily moved when the core member 20 is disposed in the lumen 11.

The material of the core member 20 is preferably a metal, and the material of the tubular member 30 is preferably a resin composition containing polyethylene as a main component. In a case where the material of the core member 20 is a metal, and the material of the tubular member 30 is a resin composition containing polyethylene as a main component, the core member 20 is easily fixed to the shaft 10 through the tubular member 30, and stiffness of the shaft 10 can be sufficiently enhanced in a portion in which the core member 20 is disposed.

Particularly, the material of the core member 20 is more preferably Ni—Ti alloy or stainless steel-based metal, and the material of the tubular member 30 is more preferably high-density polyethylene resin. In a case where the material of the core member 20 is Ni—Ti alloy or stainless steel-based metal, and the material of the tubular member 30 is high-density polyethylene resin, the core member 20 and the lumen 11 are easily adhered to each other through the tubular member 30, and a strength of adhesion between the core member 20 and the lumen 11 can also be enhanced.

FIG. 4 is a cross-sectional view, along the longitudinal direction, of the medical shaft 1 according to another embodiment of the present invention. As shown in FIG. 4, an outer diameter D1 of the shaft 10 in the portion in which the tubular member 30 is disposed is preferably greater than an outer diameter D2 of the shaft 10 at a portion closer to the distal side than a distal end 30*d* of the tubular member 30 is, and is preferably greater than an outer diameter D3 of the shaft 10 at a portion closer to the proximal side than a proximal end 30*p* of the tubular member 30 is. In a case where the lumen 11 is press-widened by the tubular member 30, a thickness of the shaft 10 in the portion in which the tubular member 30 is disposed may be reduced. Since the strength of the shaft 10 is reduced in the portion in which the thickness of the shaft 10 is reduced, damage may occur when, for example, the medical shaft 1 is being manufactured or used. Therefore, the outer diameter D1 of the shaft 10 in the portion in which the tubular member 30 is disposed is made greater than the outer diameter D2 of the shaft 10 at the portion closer to the distal side than the distal end 30*d* of the tubular member 30 is, and made greater than the outer diameter D3 of the shaft 10 at the portion closer to the proximal side than the proximal end 30*p* of the tubular member 30 is, whereby the thickness of the shaft 10 in the portion in which the tubular member 30 is disposed is increased and strength can be enhanced.

Examples of a method in which the outer diameter D1 of the shaft 10 in the portion in which the tubular member 30 is disposed is made greater than the outer diameter D2 of the shaft 10 at the portion closer to the distal side than the distal end 30*d* of the tubular member 30 is and made greater than the outer diameter D3 of the shaft 10 at the portion closer to the proximal side than the proximal end 30*p* of the tubular member 30 is, include a method in which a tubular member containing the same material as the material of the shaft 10 is disposed outward of the shaft 10 in the portion in which the tubular member 30 is disposed, and the shaft 10 and the tubular member are integrated with each other by, for example, thermal welding.

In a case where the outer diameter D1 of the shaft 10 in the portion in which the tubular member 30 is disposed is greater than the outer diameter D2 of the shaft 10 at the portion closer to the distal side than the distal end 30*d* of the tubular member 30 is and is greater than the outer diameter D3 of the shaft 10 at the portion closer to the proximal side than the proximal end 30*p* of the tubular member 30 is, the outer diameter D1 is preferably not greater than 1.1 times each of the outer diameter D2 and the outer diameter D3, more preferably not greater than 1.05 times each of the outer diameter D2 and the outer diameter D3, and even more preferably not greater than 1.01 times each of the outer diameter D2 and the outer diameter D3. In a case where the upper limit value of a ratio in size between the outer diameter D1 and each of the outer diameter D2 and the outer diameter D3 is set in the above-described range, a large stepped portion is unlikely to be generated between the portion of the shaft 10 having the outer diameter D1 and having the tubular member 30 disposed therein, and each of the portion of the shaft 10 which has the outer diameter D2 and is closer to the distal side than the distal end 30*d* of the tubular member 30 is and the portion of the shaft 10 which has the outer diameter D3 and is closer to the proximal side than the proximal end 30*p* of the tubular member 30 is, and the shaft 10 is unlikely to be caught when the medical shaft 1 is inserted in a lumen, and the medical shaft 1 can have high insertability.

Further, although it is not shown in the drawings, it is also preferable that the outer diameter D1 of the shaft 10 in the portion in which the tubular member 30 is disposed is less than the outer diameter D2 of the shaft 10 at the portion closer to the distal side than the distal end 30*d* of the tubular member 30 is and is less than the outer diameter D3 of the shaft 10 at the portion closer to the proximal side than the proximal end 30*p* of the tubular member 30 is. In a case where the outer diameter D1 of the shaft 10 in the portion in which the tubular member 30 is disposed is less than the outer diameter D2 of the shaft 10 at the portion closer to the distal side than the distal end 30*d* of the tubular member 30 is and is less than the outer diameter D3 of the shaft 10 at the portion closer to the proximal side than the proximal end 30*p* of the tubular member 30 is, the shaft 10 in the portion in which the tubular member 30 is disposed is unlikely to come into contact with another object, and, furthermore, the outer surface of the shaft 10 is unlikely to protrude, whereby insertability of the medical shaft 1 can be enhanced.

Examples of a method in which the outer diameter D1 of the shaft 10 in the portion in which the tubular member 30 is disposed is made less than the outer diameter D2 of the shaft 10 at the portion closer to the distal side than the distal end 30*d* of the tubular member 30 is and made less than the outer diameter D3 of the shaft 10 at the portion closer to the proximal side than the proximal end 30*p* of the tubular member 30 is, include a method in which a heat-shrinkable tube is disposed outward of the shaft 10 in the portion in which the tubular member 30 is disposed, and the heat-shrinkable tube is heated and shrunk to reduce the outer diameter of the shaft 10 in the portion in which the tubular member 30 is disposed.

In a case where the outer diameter D1 of the shaft 10 in the portion in which the tubular member 30 is disposed is less than the outer diameter D2 of the shaft 10 at the portion closer to the distal side than the distal end 30*d* of the tubular member 30 is, and is less than the outer diameter D3 of the shaft 10 at the portion closer to the proximal side than the proximal end 30*p* of the tubular member 30 is, the outer diameter D1 is preferably not less than 0.9 times each of the outer diameter D2 and the outer diameter D3, more preferably not less than 0.95 times each of the outer diameter D2 and the outer diameter D3, and even more preferably not less than 0.97 times each of the outer diameter D2 and the outer diameter D3. In a case where the lower limit value of a ratio in size between the outer diameter D1 and each of the outer diameter D2 and the outer diameter D3 is set in the above-described range, strength of the shaft 10 can be assured in the portion in which the tubular member 30 is disposed.

In the lumen 11, a length L1 of the major axis of the cross-section of the tubular member 30 on the plane perpendicular to the longitudinal direction in the portion in which the tubular member 30 is disposed as shown in FIG. 2, is preferably greater than a length L2 of the major axis of the cross-section of the lumen 11 on the plane perpendicular to the longitudinal direction in the portion in which the tubular member 30 is not disposed as shown in FIG. 3. In the portion in which the tubular member 30 is disposed, the outer surface of the tubular member 30 is pressed against the circumferential wall of the shaft 10, and the lumen 11 is press-widened by the tubular member 30. Therefore, the length L1 of the major axis of the cross-section of the tubular member 30 on the plane perpendicular to the longitudinal direction in the portion in which the tubular member 30 is disposed is greater than the length L2 of the major axis of the cross-section of the lumen 11 on the plane perpendicular to the longitudinal direction in the portion in which the tubular member 30 is not disposed. Since the length L1 of the major axis of the cross-section of the tubular member 30 in the portion in which the tubular member 30 is disposed is greater than the length L2 of the major axis of the cross-section of the lumen 11 in the portion in which the tubular member 30 is not disposed, the tubular member 30 comes into close contact with the circumferential wall of the lumen 11. Therefore, strength of joining the shaft 10 and the tubular member 30 to each other can be enhanced.

The "major axis of the cross-section of the tubular member 30" represents an axis having the maximum length and passing through a center P1 of the cross-section of the tubular member 30 and two points (P2, P3) on the outer shape of the cross-section of the tubular member 30 on the plane perpendicular to the longitudinal direction in the portion in which the tubular member 30 is disposed, as shown in FIG. 2. The "major axis of the cross-section of the lumen 11" represents an axis having the maximum length and passing through a center P4 of the cross-section of the lumen 11 and two points (P5, P6) on the circumferential wall of the cross-section of the lumen 11 on the plane perpendicular to the longitudinal direction in the portion in which the tubular member 30 is disposed, as shown in FIG. 3.

The length L1 of the major axis of the cross-section of the tubular member 30 on the plane perpendicular to the longitudinal direction in the portion in which the tubular member 30 is disposed is preferably not less than 1.05 times the length L2 of the major axis of the cross-section of the lumen 11 on the plane perpendicular to the longitudinal direction in the portion in which the tubular member 30 is not disposed, more preferably not less than 1.1 times the length L2, and even more preferably not less than 1.15 times the length L2. In a case where the lower limit value of the ratio between the length L1 of the major axis of the cross-section of the tubular member 30 in the portion in which the tubular member 30 is disposed and the length L2 of the major axis of the cross-section of the lumen 11 in the portion in which the tubular member 30 is not disposed is set in the above-described range, the tubular member 30 can be sufficiently brought into close contact with the circumferential wall of the lumen 11. As a result, the tubular member 30 and the shaft 10 can be firmly joined to each other. The length L1 of the major axis of the cross-section of the tubular member 30 on the plane perpendicular to the longitudinal direction in the portion in which the tubular member 30 is disposed is preferably not greater than 1.5 times the length L2 of the major axis of the cross-section of the lumen 11 on the plane perpendicular to the longitudinal direction in the portion in which the tubular member 30 is not disposed, more preferably not greater than 1.4 times the length L2, and even more preferably not greater than 1.3 times the length L2. The upper limit value of the ratio between the length L1 of the major axis of the cross-section of the tubular member 30 in the portion in which the tubular member 30 is disposed and the length L2 of the major axis of the cross-section of the lumen 11 in the portion in which the tubular member 30 is not disposed is set in the above-described range, the length L1 of the major axis of the cross-section of the tubular member 30 is prevented from becoming excessively great relative to the length L2 of the major axis of the cross-section of the lumen 11, and the tubular member 30 can be easily disposed in the lumen 11.

The length of the tubular member 30 in the longitudinal direction is preferably not greater than 1/10 of the length of the core member 20. In a case where the length of the tubular member 30 is not greater than 1/10 of the length of the core member 20, when the core member 20 and the shaft 10 are joined to each other, the length of the tubular member 30 is not excessively great, and the tubular member 30 is easily disposed on the outer side of the core member 20 and disposed inside the lumen 11. Although the length of the tubular member 30 in the longitudinal direction is preferably not greater than 1/10 of the length of the core member 20, also in a case where the length of the tubular member 30 is greater than 1/10 of the length of the core member 20, the medical shaft 1 can be manufactured, and the medical shaft 1 according to this aspect is also included in the present invention.

The length of the tubular member 30 in the longitudinal direction is preferably not greater than 1/10 of the length of the core member 20, more preferably not greater than 1/11 thereof, and even more preferably not greater than 1/12 thereof. In a case where the upper limit value of the ratio between the length of the tubular member 30 and the length of the core member 20 is set in the above-described range, the tubular member 30 can be easily disposed on the outer side of the core member 20, and efficiency for manufacturing the medical shaft 1 can be enhanced. The length of the tubular member 30 in the longitudinal direction is preferably about 2 mm to 5 mm. If the length of the tubular member 30 is small, the strength for fixing the core member 20 becomes low. If the length of the tubular member 30 is great, the portion in which the tubular member 30 is disposed becomes harder than the other portion. The length of the tubular member 30 in the longitudinal direction can be selected according to the length of the core member 20, a required fixing strength, materials of the members, and the like.

A plurality of the tubular members 30 may be disposed at different positions in the lumen 11 of the shaft 10. For example, in a case where the tubular members 30 are disposed in the lumen 11 at two positions in total such as the distal side portion and the proximal side portion of the shaft 10, the entirety of the core member 20 and the shaft 10 are joined to each other, and stiffness can be imparted to the medical shaft 1.

Next, a method for manufacturing the medical shaft 1 of the present invention will be described. In the following description, the same description as the above description is omitted.

FIG. 5 is a cross-sectional view, along the longitudinal direction, of the medical shaft 1 in a state where the core member 20 is disposed in the lumen 11 of the shaft 10. FIG. 6 is a cross-sectional view, along the longitudinal direction, of the medical shaft 1 in a state where an outer tubular member 40 is disposed outward of the shaft 10 in a portion in which the tubular member 30 is disposed. FIG. 7 is a cross-sectional view, along the longitudinal direction, of the medical shaft 1 in a state of having an opening 50 through which the lumen 11 and a portion outside the shaft 10 are connected. FIG. 8 is a view, along the longitudinal direction, of the medical shaft 1 in a state where the shaft 10 has a flap 51 formed therein.

As shown in FIG. 5, a method for manufacturing the medical shaft 1 includes a step (hereinafter, may also be referred to as "core member step") of disposing, in the lumen 11 of the shaft 10, the core member 20 on which the tubular member 30 is not disposed, a step (hereinafter, may also be referred to as "tubular member step") of disposing the core member 20 inside the tubular member 30, and a step (hereinafter, may also be referred to as "heating step") of heating the tubular member 30. The tubular member 30 is disposed between the shaft 10 and the core member 20, and the length of the tubular member 30 in the longitudinal direction is less than the length of the core member 20.

The tubular member step is preferably performed after the core member step. That is, the step of disposing the core member 20 inside the tubular member 30 is preferably performed after the step of disposing the core member 20 in the lumen 11 of the shaft 10. By performing the tubular member step after the core member step, the core member 20 can be easily inserted in the lumen 11 and the tubular member 30 can be easily disposed at a desired position in the lumen 11. As a result, efficiency of manufacturing the medical shaft 1 can be enhanced. The tubular member step is, in other words, a step of disposing the tubular member 30 radially outward of the core member 20. The tubular member step is, for example, a step of inserting the core member 20 in a lumen of the tubular member 30. Through the tubular member step, the tubular member 30 can be disposed in the same lumen 11 as the lumen 11 in which the core member 20 is disposed, among the lumens 11 of the shaft 10. As a result, the tubular member 30 is disposed around the core member 20.

The heating step is preferably performed after the tubular member step and the core member step. That is, the step of heating the tubular member 30 is preferably performed after the step of disposing the core member 20 inside the tubular member 30 and the step of disposing the core member 20 in the lumen 11 of the shaft 10. The core member 20 on which the tubular member 30 is disposed needs to be disposed in the lumen 11 of the shaft 10 before the heating step. By performing the heating step after the tubular member step and the core member step, the tubular member 30 having been heated and melted is adhered to both the core member 20 and the circumferential wall of the lumen 11. Therefore, the shaft 10 and the core member 20 can be efficiently joined to each other through the tubular member 30.

The heating step of heating the tubular member 30 may be a step of heating the shaft 10 in the portion in which the tubular member 30 is disposed. By heating the shaft 10 in the portion in which the tubular member 30 is disposed, heat is transmitted to the tubular member 30, and the tubular member 30 having been melted is adhered to both the core member 20 and the circumferential wall of the lumen 11. In the heating step, the shaft 10 is preferably heated at a temperature of not higher than a melting point of the shaft 10 and not lower than a melting point of the tubular member 30. In a case where a time of the heating step is short, the heating temperature may be higher than the melting point of the shaft 10. The heating temperature may be a temperature of not higher than the melting point of the tubular member 30 in a case where the tubular member 30 is sufficiently softened. The materials of the shaft 10 and the tubular member 30 can be selected based on the melting points. The heating time can be selected as appropriate according to the materials of the shaft 10 and the tubular member 30 and the heating temperature. A melting point of a material of the outer tubular member 40 described below may be a temperature higher than the melting point of the tubular member 30. By checking the melting state of the outer tubular member 40, sufficient heating for melting the tubular member 30 can be determined, and a step of joining the shaft 10 and the core member 20 through the tubular member 30 can be stabilized.

Before the step of disposing the core member 20 in the lumen 11 of the shaft 10, the outer diameter of the tubular member 30 is preferably greater than the inner diameter of the lumen 11. In a case where the outer diameter of the tubular member 30 is greater than the inner diameter of the lumen 11 before the core member step, when the core member 20 and the tubular member 30 are disposed in the lumen 11, the outer surface of the tubular member 30 and the circumferential wall of the lumen 11 easily come into close contact with each other. Therefore, strength of joining the tubular member 30 and the shaft 10 to each other can be enhanced.

In a case where the cross-sectional shape, of the outer shape of the tubular member 30, perpendicular to the longitudinal direction is not round, the "outer diameter of the tubular member 30" is a "length of the major axis of the cross-sectional shape of the tubular member 30". In a case where the cross-sectional shape, of the lumen 11, perpendicular to the longitudinal direction is not round, the "inner diameter of the lumen 11" is a "length of the major axis of the cross-sectional shape of the lumen 11".

Before the core member step, the outer diameter of the tubular member 30 is preferably not less than 1.05 times the inner diameter of the lumen 11, more preferably not less than 1.1 times the inner diameter of the lumen 11, and even more preferably not less than 1.15 times the inner diameter of the lumen 11. In a case where the lower limit value of a ratio between the outer diameter of the tubular member 30 and the inner diameter of the lumen 11 is set in the above-described range before the core member step, the outer surface of the tubular member 30 easily comes into close contact with the circumferential wall of the lumen 11 when the tubular member 30 is disposed in the lumen 11. Before the core member step, the outer diameter of the tubular member 30 is preferably not greater than 1.3 times the inner diameter of the lumen 11, more preferably not greater than 1.25 times the inner diameter of the lumen 11, and even more preferably not greater than 1.2 times the inner diameter of the lumen 11. In a case where the upper limit value of the ratio between the outer diameter of the tubular member 30 and the inner diameter of the lumen 11 is set in the above-described range before the core member step, the tubular member 30 can be easily disposed in the lumen 11.

As shown in FIG. 6, after the step of disposing the core member 20 inside the tubular member 30 and the step of disposing, in the lumen 11 of the shaft 10, the core member 20 on which the tubular member 30 is disposed, a step (hereinafter, may also be referred to as "outer tubular member step") of disposing the outer tubular member 40 outward of the shaft 10 in the portion in which the tubular member 30 is disposed is preferably performed. As described above, in a case where the tubular member 30 is disposed in the lumen 11, the lumen 11 is press-widened by the tubular member 30, the thickness of the shaft 10 is reduced in the portion in which the tubular member 30 is disposed, strength of the shaft 10 is reduced in the portion in which the thickness of the shaft 10 is reduced, and damage is likely to be caused. In a case where the outer tubular member step is performed after the tubular member step and the core member step, the outer tubular member 40 is disposed outward of the shaft 10 in the portion in which the tubular member 30 is disposed and the thickness of the shaft 10 tends to be reduced. Therefore, even when the thickness of the shaft 10 is reduced in the portion in which the tubular member 30 is disposed, this portion is protected by the outer tubular member 40 to prevent damage to the shaft 10, thereby enhancing durability of the medical shaft 1.

A step (hereinafter, may also be referred to as "protective core member step") of disposing a protective core member in an empty lumen may be performed. In a case where the protective core member is disposed in the empty lumen, the length of the major axis of the cross-sectional shape of the empty lumen can be assured. When the shaft 10 is heated in order to join the shaft 10 and the core member 20 to each other, escape of stress in melting or softening the shaft 10 is prevented and the tubular member 30 comes into closer contact with the core member 20 to enhance joining strength.

Examples of a material of the outer tubular member 40 include polyamide-based resins, polyester-based resins such as polyethylene terephthalate, polyurethane-based resins, polyolefin-based resins such as polyethylene and polypropylene, fluorine-based resins such as polytetrafluoroethylene, vinyl chloride-based resins, silicone-based resins, and natural rubber. One of them may be used alone or two or more of them may be used in combination.

Among them, the material of the outer tubular member 40 is preferably the same as the material of the shaft 10 or preferably contains the same material as the material of the shaft 10. In a case where the material of the outer tubular member 40 is the same as the material of the shaft 10 or contains the same material as the material of the shaft 10, the outer tubular member 40 and the shaft 10 are melted and integrated with each other by heating the outer tubular member 40 after the outer tubular member 40 is disposed outward of the shaft 10, thereby preventing the outer tubular member 40 from being detached from the shaft 10 and increasing the thickness of the shaft 10 in the portion in which the tubular member 30 is disposed.

The cross-sectional shape of the outer tubular member 40 in the longitudinal direction may be a C-shape or a rolled shape. The cross-sectional shape of the outer shape of the outer tubular member 40 in the longitudinal direction may be a round shape, an ellipsoidal shape, a polygonal shape, or a combination thereof.

As shown in FIG. 6, a length L3 of the tubular member 30 in the longitudinal direction may be less than a length L4 of the outer tubular member 40. In a case where the length L3 of the tubular member 30 is less than the length L4 of the outer tubular member 40, the entirety of the portion in which the shaft 10 has a reduced thickness due to the tubular member 30 being disposed in the lumen 11 can be covered by the outer tubular member 40. Therefore, the entirety of the portion in which the shaft 10 has the reduced thickness can be protected by the outer tubular member 40, and durability of the medical shaft 1 can be enhanced. The length L3 of the tubular member 30 in the longitudinal direction may be greater than the length L4 of the outer tubular member 40. In a case where the length L3 of the tubular member 30 is greater than the length L4 of the outer tubular member 40, the portion in which the tubular member 30 is disposed can be reinforced. In a case where, when the flap 51 described below is disposed at the shaft 10, the opening 50 is covered by the flap 51, or in a case where a portion of the shaft 10 which is removed in order to form the opening 50 described below or a piece material containing the same material as that of the shaft 10 is disposed in the opening 50, the outer tubular member 40 can press the entirety of the piece material or the flap 51 against the opening 50 by making the length L3 of the tubular member 30 greater than the length L4 of the outer tubular member 40.

In a case where the length L3 of the tubular member 30 is less than the length L4 of the outer tubular member 40, the length L3 of the tubular member 30 in the longitudinal direction is preferably not greater than 0.9 times the length L4 of the outer tubular member 40, more preferably not greater than 0.8 times the length L4, and even more preferably not greater than 0.7 times the length L4. In a case where the upper limit value of a ratio between the length L3 of the tubular member 30 and the length L4 of the outer tubular member 40 is set in the above described range, the entirety of the tubular member 30 can be easily covered by the outer tubular member 40, and the entirety of the portion in which the shaft 10 has the reduced thickness due to the tubular member 30 being disposed in the lumen 11 can be easily protected by the outer tubular member 40. The length L3 of the tubular member 30 in the longitudinal direction is preferably not less than 0.1 times the length L4 of the outer tubular member 40, more preferably not less than 0.2 times the length L4, and even more preferably not less than 0.3 times the length L4. In a case where the lower limit value of a ratio between the length L3 of the tubular member 30 and the length L4 of the outer tubular member 40 is set in the above-described range, the outer tubular member 40 is prevented from becoming excessively long and the outer tubular member step can be easily performed.

In a case where the length L3 of the tubular member 30 is greater than the length L4 of the outer tubular member 40, the length L3 of the tubular member 30 in the longitudinal direction may be greater than or equal to 1.1 times the length L4 of the outer tubular member 40, is more preferably greater than or equal to 1.2 times the length L4, and may be greater than or equal to 1.3 times the length L4. In a case where the outer tubular member is made longer than the tubular member 30, and the lower limit value of a ratio between the length L3 of the tubular member 30 and the length L4 of the outer tubular member 40 is set in the above-described range, a melting state of the outer tubular member 40 can be used as an index for determining a degree of joining of the tubular member 30, and the heating step can be stabilized and easily performed. The length L3 of the tubular member 30 in the longitudinal direction is preferably not greater than 2.0 times the length L4 of the outer tubular member 40, more preferably not greater than 1.9 times the length L4, and even more preferably not greater than 1.8 times the length L4. In a case where the upper limit value of a ratio between the length L3 of the tubular member 30 and the length L4 of the outer tubular member 40 is set in the above-described range, the length of the outer tubular member 40 is prevented from becoming excessively long and the outer tubular member step can be easily performed.

Before the heating step, a step (hereinafter, may also be referred to as "heat-shrinkable tube step") of disposing a heat-shrinkable tube outward of the shaft 10 may be performed, which is not shown. When the tubular member 30 is melted in the heating step, the tubular member 30 having been melted may flow to enlarge the outer diameter of a part of the shaft 10. In a case where the heat-shrinkable tube is disposed outward of the shaft 10, the heat-shrinkable tube is also heated in the heating step and the diameter of the heat-shrinkable tube is reduced. As a result, the outer diameter of the shaft 10 in a portion in which the heat-shrinkable tube is disposed is prevented from being enlarged, and the medical shaft 1 in which unevenness is small on the outer surface can be manufactured.

The step of heating the tubular member is preferably performed after the step of disposing the heat-shrinkable tube outward of the shaft 10, and the step (hereinafter, may also be referred to as "removal step") of removing the heat-shrinkable tube is preferably performed after the step of heating the tubular member. In a case where the heating step is performed after the heat-shrinkable tube step, and, furthermore, the removal step is thereafter performed, the outer diameter of the shaft 10 is prevented from being enlarged by the tubular member 30 and, furthermore, unevenness of the outer surface of the shaft 10 and reduction of slidability due to the heat-shrinkable tube being disposed outward of the shaft 10 are prevented, and insertability of the medical shaft 1 can be enhanced.

After the step of heating the tubular member 30, a step (hereinafter, may also be referred to as "post-heating processing step") of heating the shaft 10 at a temperature of not lower than 50° C. for two hours or longer is preferably performed. By performing the post-heating processing step after the heating step, close contact between the tubular member 30 and the core member 20, and close contact between the tubular member 30 and the shaft 10, which have been joined to each other in the heating step, can be performed with enhanced effectiveness, and close contact between the outer tubular member 40 and the shaft 10 can be performed with enhanced effectiveness. By performing the post-heating processing step, the unevenness of the surface of the shaft 10 generated in manufacturing the medical shaft 1 can be reduced, and the surface of the medical shaft 1 can be made smooth to enhance insertability.

In the post-heating processing step, the shaft 10 is preferably heated at a temperature of not lower than 50° C., and the heating temperature for the shaft 10 is more preferably not lower than 50.5° C., and even more preferably not lower than 51° C. In a case where the lower limit value of the heating temperature for the shaft 10 in the post-heating processing step is set in the above-described range, the heating treatment of the shaft 10 can be efficiently performed. The heating temperature for the shaft 10 in the post-heating processing step is preferably not higher than 58° C., more preferably not higher than 55° C., and even more preferably not higher than 53° C. In a case where the upper limit value of the heating temperature for the shaft 10 in the post-heating processing step is set in the above-described range, the shaft 10 and the tubular member 30 or the tubular member 30 and the core member 20 can be prevented from being unjoined due to the shaft 10 or the tubular member 30 having an excessively high temperature and being melted again.

In the post-heating processing step, the shaft 10 is preferably heated for two hours or longer, and the heating time of the shaft 10 is more preferably not less than 2.3 hours and even more preferably not less than 2.5 hours. In a case where the lower limit value of the heating time of the shaft 10 in the post-heating processing step is set in the above-described range, the entirety of the shaft 10 can be sufficiently heated and the heating treatment can be sufficiently performed. In the post-heating processing step, the heating time of the shaft 10 is preferably not longer than 11 hours, more preferably not longer than 10.7 hours, and even more preferably not longer than 10.5 hours. In a case where the upper limit value of the heating time of the shaft 10 in the post-heating processing step is set in the above-described range, the time required for the post-heating processing step can be shortened while the heat treatment is sufficiently performed. Therefore, efficiency for manufacturing the medical shaft 1 can be enhanced.

Preferably, the method for manufacturing the medical shaft 1 of the present invention further includes a step (hereinafter, may also be referred to as "opening step") of forming the opening 50 through which a portion outside the shaft 10 and the lumen 11 are connected, as shown in FIG. 7. In a case where the shaft 10 has the opening 50, the end portion of the core member 20 disposed in the lumen 11 can be extracted through the opening 50, and the tubular member 30 can be disposed on the core member 20 exposed to the outside. Thus, the tubular member step can be performed more easily as compared with a case where the core member 20 on which the tubular member 30 is disposed radially outward thereof is disposed in the lumen 11. In a case where a step of extracting the core member 20 through the opening 50 and disposing the tubular member 30 is performed, the outer diameter of the tubular member 30 can be enlarged and close contact between the circumferential wall of the lumen 11 and the tubular member 30 can be performed with enhanced effectiveness.

Examples of the opening step include forming a through hole in the shaft 10 to form the opening 50 through which the lumen 11 and a portion outside the shaft 10 are connected to each other, and cutting the outer surface of the shaft 10 to form the opening 50 through which the lumen 11 and a portion outside the shaft 10 are connected to each other. Preferably, in a case where the opening 50 is formed in the shaft 10, before the heating step is performed, a portion of the shaft 10 which is removed in order to form the opening 50, or a piece material containing the same material as that of the shaft 10, is disposed in the opening 50, and heating is then performed.

The size of the opening 50 in the longitudinal direction is preferably longer than the length of the tubular member 30. In a case where the size of the opening 50 is longer than the length of the tubular member 30, the end portion of the core member 20 disposed in the lumen 11 can be easily extracted through the opening 50, the tubular member 30 can be easily disposed on the core member 20 having been extracted through the opening 50, and the core member 20 having the tubular member 30 disposed radially outward thereof can be easily inserted in the opening 50. Therefore, efficiency for manufacturing the medical shaft 1 can be enhanced.

The size of the opening 50 in the longitudinal direction is preferably not less than 1.1 times the length of the tubular member 30, more preferably not less than 1.2 times the length of the tubular member 30, and even more preferably not less than 1.3 times the length of the tubular member 30. In a case where the lower limit value of a ratio between the size of the opening 50 and the length of the tubular member 30 is set in the above-described range, extraction of the end portion of the core member 20 through the opening 50 and insertion of the core member 20 through the opening 50 are facilitated. The size of the opening 50 in the longitudinal direction is preferably not greater than three times the length of the tubular member 30, more preferably not greater than 2.5 times the length of the tubular member 30, and even more preferably not greater than twice the length of the tubular member 30. In a case where the upper limit value of the ratio between the size of the opening 50 and the length of the tubular member 30 is set in the above-described range, the size of the opening 50 is prevented from being excessively large, the joined portion can be accurately set, and the strength of the shaft 10 can be made sufficient.

As shown in FIG. 8, the flap 51 in which one of end portions is a free end and the other of the end portions is integrated with the shaft 10 is preferably formed by cutting the outer surface of the shaft 10 in the step of forming the opening 50. By forming the flap 51 in the opening step, the opening 50 can be covered by the flap 51. Therefore, after the core member step is performed such that the end portion of the core member 20 disposed in the lumen 11 is extracted through the opening 50, the tubular member 30 is disposed, and the tubular member 30 is disposed in the lumen 11, the opening 50 is covered by the flap 51 and the heating step is thereafter performed, thereby closing the opening 50. As a result, an area in which the tubular member 30 and the shaft 10 are in contact with each other can be increased, whereby the strength of joining the core member 20 and the shaft 10 to each other through the tubular member 30 can be enhanced.

The length of the flap 51 in the longitudinal direction from one of the end portions to the other of the end portions is preferably greater than the length of the tubular member 30. In a case where the length of the flap 51 is greater than the length of the tubular member 30, contact between the flap 51 and the entire length of the tubular member 30 in the longitudinal direction is facilitated, and the tubular member 30 and the shaft 10 are firmly joined to each other. As a result, the core member 20 can be firmly joined to the shaft 10 through the tubular member 30.

The length of the flap 51 in the longitudinal direction from the one of the end portions to the other of the end portions is preferably not less than 1.1 times the length of the tubular member 30, more preferably not less than 1.2 times the length of the tubular member 30, and even more preferably not less than 1.3 times the length of the tubular member 30. In a case where the lower limit value of a ratio between the length of the tubular member 30 and the length of the flap

51 from the one of the end portions to the other of the end portions is set in the above-described range, the flap 51 easily comes into contact with the entire length of the tubular member 30 in the longitudinal direction, and strength of joining the shaft 10 and the core member 20 to each other through the tubular member 30 is likely to be enhanced. The length of the flap 51 in the longitudinal direction from the one of the end portions to the other of the end portions is preferably not greater than three times the length of the tubular member 30, more preferably not greater than 2.5 times the length of the tubular member 30, and even more preferably not greater than twice the length of the tubular member 30. In a case where the upper limit value of the ratio between the length of the tubular member 30 and the length of the flap 51 from the one of the end portions to the other of the end portions is set in the above-described range, reduction of the strength due to increase of the length of the flap 51 can be prevented. Therefore, the flap 51 is not easily broken when the medical shaft 1 is manufactured, and efficiency for manufacturing the medical shaft 1 can be enhanced.

Preferably, the method for manufacturing the medical shaft 1 of the present invention further includes a step of disposing the core member 20 in the lumen 11 of the shaft 10 before the step of disposing the core member 20 inside the tubular member 30, and the step of forming the opening 50 is performed after the step of disposing the core member 20 in the lumen 11 of the shaft 10, and the outer surface of the shaft 10 is cut in the step of forming the opening 50 in a state where the core member 20 is disposed in the lumen 11. In a case where the outer surface of the shaft 10 is cut in the opening step after the core member step in a state where the core member 20 is disposed in the lumen 11, the depth by which the outer surface of the shaft 10 is cut can be defined. Specifically, in a case where the outer surface of the shaft 10 is deeply cut by a cutting tool or the like in a state where the core member 20 is disposed in the lumen 11, the cutting tool or the like abuts against the core member 20 to stop the progress of the cutting tool or the like, thereby preventing the shaft 10 from being excessively deeply cut. Therefore, the opening 50 through which the lumen 11 having the core member 20 disposed therein is connected to a portion outside the shaft 10 can be easily formed and efficiency for manufacturing the medical shaft 1 can be enhanced.

In the opening step, although the core member 20 may be disposed in the lumen 11 when the outer surface of the shaft 10 is cut, it is also preferable that a tool for forming the opening 50 is disposed. By using the tool for forming the opening 50, defect is not generated in the core member 20, and the shape, the material, and the like of the tool can be made proper for forming the opening 50. Therefore, in a case where the outer surface of the shaft 10 is cut in the opening step in a state where the tool is disposed in the lumen 11, efficiency for forming the opening 50 can be further enhanced. Examples of a material of the tool for forming the opening 50 include stainless steel such as SUS and carbon steel.

As described above, the medical shaft of the present invention includes: the shaft including at least one lumen extending in the longitudinal direction; the core member which is disposed in the lumen and which extends along the longitudinal direction; and the tubular member which is disposed on an outer side of the core member in the same lumen as a lumen in which the core member is disposed and which has a length, in the longitudinal direction, which is less than a length of the core member. In the lumen, an area of a cross-section of the lumen on a plane perpendicular to the longitudinal direction in a portion in which the tubular member is disposed is greater than an area of a cross section of the lumen on a plane perpendicular to the longitudinal direction in a portion in which the tubular member is not disposed. In a case where the area of the cross-section of the lumen on the plane perpendicular to the longitudinal direction in the portion in which the tubular member is disposed is greater than the area of the cross-section of the lumen on the plane perpendicular to the longitudinal direction in the portion in which the tubular member is not disposed, the outer surface of the tubular member is pressed against the wall surface of the lumen of the shaft in the portion in which the tubular member is disposed. Therefore, the tubular member easily comes into close contact with the wall surface of the lumen of the shaft, and the core member and the shaft can be firmly joined to each other through the tubular member.

The method of the present invention for manufacturing the medical shaft is a method for manufacturing the medical shaft that includes: the shaft including at least one lumen extending in the longitudinal direction; the core member which is disposed in the lumen and which extends along the longitudinal direction; and the tubular member which is disposed between the shaft and the core member in the same lumen as a lumen in which the core member is disposed and which has a length, in the longitudinal direction, which is less than a length of the core member, and the method includes: disposing, in the lumen of the shaft, the core member on which the tubular member is not disposed; disposing the core member inside the tubular member; and heating the tubular member. The step of disposing the core member in the lumen of the shaft, the step of disposing the core member inside the tubular member, and the step of heating the tubular member are performed, whereby the core member and the shaft can be easily joined firmly to each other through the tubular member.

This application claims priority to Japanese Patent Application No. 2020-30645, filed on Feb. 26, 2020. All of the contents of the Japanese Patent Application No. 2020-30645, filed on Feb. 26, 2020, are incorporated by reference herein.

REFERENCE SIGNS LIST

1: medical shaft
10: shaft
11: lumen
20: core member
30: tubular member
30*d*: distal end
30*p*: proximal end
40: outer tubular member
50: opening
51: flap
P1: center of the cross-section of the tubular member
P2: point on the outer shape of the cross-section of the tubular member
P3: point on the outer shape of the cross-section of the tubular member
P4: center of the cross-section of the lumen
P5: points on the circumferential wall of the cross-section of the lumen
P6: points on the circumferential wall of the cross-section of the lumen
L1: length of the major axis of the cross-section of the tubular member L2: length of the major axis of the cross-section of the lumen L3: length of the tubular member L4: length of the outer tubular member D1: outer diameter of the shaft in the portion in which the tubular member D2: outer diameter of the shaft at a portion closer to the distal side than a distal end of the tubular member D3: outer diameter of the shaft at a portion closer to the proximal side than a proximal end of the tubular member

The invention claimed is:

1. A method for manufacturing a medical shaft comprising a shaft including at least one lumen extending in a longitudinal direction, a core member disposed in the lumen, the core member extending along the longitudinal direction, and a tubular member disposed between the shaft and the core member in a same lumen as a lumen in which the core member is disposed, the tubular member having a length, in the longitudinal direction, which is shorter than a length of the core member, the method comprising the steps of:

forming an opening through which the lumen and a portion outside the shaft are connected;

disposing, in the lumen of the shaft, the core member on which the tubular member is not disposed;

disposing the core member inside the tubular member;

disposing the tubular member in the lumen of the shaft; and then heating the tubular member so that the tubular member is adhered to the core member and a circumferential wall of the lumen of the shaft, wherein the opening is closed by the heating, and wherein the steps are performed in the order as recited.

2. The method for manufacturing the medical shaft according to claim 1, wherein an outer diameter of the tubular member is greater than an inner diameter of the lumen of the shaft before the disposing of the core member in the lumen of the shaft.

3. The method for manufacturing the medical shaft according to claim 1, further comprising disposing an outer tubular member to cover an outer surface of the shaft at a portion, in which the tubular member is disposed, after the core member is disposed inside the tubular member which is disposed in the lumen of the shaft.

4. The method for manufacturing the medical shaft according to claim 1, wherein the heating of the tubular member includes heating the shaft in the portion in which the tubular member is disposed.

5. The method for manufacturing the medical shaft according to claim 1, further comprising heating the shaft at a temperature of not lower than 50° C. for two hours or longer after the heating of the tubular member.

6. The method for manufacturing the medical shaft according to claim 1, wherein an outer surface of the shaft is cut to form a flap in which one of end portions is a free end and another of the end portions is integrated with the shaft, in the forming of the opening.

7. The method for manufacturing the medical shaft according to claim 1, wherein the core member is disposed in the lumen of the shaft before the core member is disposed inside the tubular member, the forming of the opening is performed after the disposing of the core member in the lumen of the shaft, and the outer surface of the shaft is cut in the forming of the opening in a state where the core member is disposed in the lumen.

8. The method for manufacturing the medical shaft according to claim 1, wherein the disposing of the core member in the lumen of the shaft is performed by inserting the core member into the lumen, and the disposing of the core member inside the tubular member is performed by inserting the core member into the tubular member.

9. The method for manufacturing the medical shaft according to claim 1, wherein the core member is disposed in the lumen of the shaft before disposing the core member inside the tubular member, the method further comprises extracting an end portion of the core member from the lumen of the shaft through the opening, passing the extracted end portion of the core member through the tubular member so that the core member is disposed inside the tubular member, and then inserting the tubular member, through which the core member has passed, into the lumen of the shaft via the opening so that the tubular member is disposed in the lumen of the shaft, before the step of heating.

* * * * *